United States Patent [19]

Ancillotti et al.

[11] 4,370,506

[45] Jan. 25, 1983

[54] TERBUTYLATING HYDROXYAROMATIC COMPOUNDS

[75] Inventors: Francesco Ancillotti, San Donato Milanese; Giuseppe Terzoni, Piacenza; Lidio Micucci, Milan; Paolo Maggioni, Montevecchia; Pietro Panseri, Bergamo, all of Italy

[73] Assignee: Anic S.p.A., Palermo, Italy

[21] Appl. No.: 286,612

[22] Filed: Jul. 24, 1981

[30] Foreign Application Priority Data

Aug. 6, 1980 [IT] Italy .................................. 24025 A/80

[51] Int. Cl.³ .............................................. C07C 37/11
[52] U.S. Cl. ....................................... 568/785; 568/784; 568/788
[58] Field of Search ................. 568/785, 766, 788, 784

[56] References Cited

U.S. PATENT DOCUMENTS 2,802,884 8/1957 D'Alelio .............................. 568/788

FOREIGN PATENT DOCUMENTS 2740590 3/1979 Fed. Rep. of Germany ...... 568/785

OTHER PUBLICATIONS

Nield Chemical Society Journal (1964) Part 2, pp. 2278–2279.

*Primary Examiner*—Werren B. Lone
*Attorney, Agent, or Firm*—Morgan, Finnegan, Pine, Foley & Lee

[57] ABSTRACT

Hydroxyaromatic compounds, especially phenols, are reacted with an alkyl tert.butyl ether in the presence of an acidic catalyst and the as formed light alcoholic fractions are removed by flashing.

4 Claims, No Drawings

TERBUTYLATING HYDROXYAROMATIC COMPOUNDS

This invention relates to a process for the terbutylation of hydroxyaromatic compounds. More particularly, this invention relates to a process for the terbutylation of phenols.

The terbutylated derivatives of hydroxyaromatic compounds, such as phenol, pyrocatechol, hydroquinone and the like are an important class of chemicals which find a practical application as antioxidants of petroleum products, monomers, food products and the like as also as intermediates for the synthesis of other derivatives. It is known that the terbutylation of a phenolic substrate is normally carried out by utilizing pure isobutene in the presence of acidic catalysts such as for example mineral acids, Friedel-Crafts catalysts and ion-exchange resins in acidic form. It is likewise known in the literature that selective terbutylations on aromatic nuclei, either activated or not, may be effected by using mixed ethers of the type

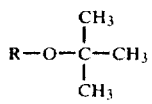

wherein R is a primary or a secondary alkyl group (Nield, J. Chem. Soc., page 2278 (1964) and DE-OS 27 40 590) and in such cases the catalysts mentioned above can be used and more particularly sulphuric acid or the ion-exchange resins having an acidic character.

The use of a mixed ether as the methyltert. butyl ether (MTBE) which is available nowadays in commercial quantities affords an improved operative convenience in comparison with the use of isobutene inasmuch as it permits to operate with a liquid rather than with a gas: in addition, to obtain a gas, expensive separation techniques are required.

The use of alkyl tert.butyl ethers, however, poses the problem of removing both the primary and the secondary alcohols which are formed during the reaction as the tert.butyl radical is being transferred onto the aromatic ring, because the effect of such alcohols is actually detrimental both when sulphuric acid and ion-exchange resins are adopted as the catalysts.

As a matter of fact, the alcohols interact with the catalyst and depress its acidity so that all a set of side reactions are hindered, which usually improve the yields of the desired product, such as the transalkylation of the ditert.butyl derivatives with the phenolic substrate, to produce monoalkyl derivatives, and such as the migration of the tert.butyl group towards positions which are thermodynamically stabler. All this has a bearing on the composition of the reaction product, which, in the presence of alcohols deriving from the ether, contains a high amount of disubstituted compounds and monosubstituted isomers which are undesirable. Since the effect of the alcohols is due to the iteraction of the alcoholic hydroxyls with the protons of the acidic groups, attempts have been made towards redressing this situation by adopting high ratios of the catalyst to the ether and high defects of the terbutylating agents with respect to the phenolic substrate, as taught by the DE-OS No. 27 40 590. This expedient, while permitting to achieve good selectivities, leads, however, to a low conversion of the phenolic substrate and brings about a considerable dehydration of the primary or the secondary alcohol with the attendant formation of a symmetrical ether and water. On the other hand, the removal of the alcohols by distillation as they are being formed, cannot be done since the alcohols generally form azeotropes with the corresponding tertbutyl ethers so that their withdrawal with such a procedure would entail an unbearable loss of terbutylating agents.

A process has now surprisingly been found, for the terbutylation of hydroxyaromatic compounds starting from alkylterbutyl ethers, whereby it becomes possible to arrive at the same selectivity and conversion as can be obtained with isobutene, while still retaining the advantages afforded by the use of liquid reactants such as the ethers aforementioned: these advantages mainly consist in the improved ease of handling of said ethers as compared with the gaseous isobutene and their lower preparation costs.

An object of the present invention is to provide a process for the terbutylation of hydroxyaromatic compounds which comprises the steps of reacting, during a first stage, said compounds with an alkyltert.butylether in a substantially stoichiometric amount or with a slight defect of a reactant whenever it is desired to boost the formation of the other, and conducting the reaction at a temperature comprised between 60° C. and 130° C. in the presence of an acidic catalyst selected from the group consisting of sulphuric acid and an ion-exchange resin such as Amberlyst 15 or Lewatit SP, a quantity of catalyst equal to 5 to 50 milliequivalents of H+ per mol of hydroxyaromatic compound being sufficient to carry out the reaction in a time comprised between 1 and 4 hours.

Under these conditions the tert.butyl groups are quantitatively transferred onto the aromatic substrate, partly in the form of the mono-tert.butyl derivative and partly in that of the di-tert.butyl derivative: at this stage it is possible to remove, by flashing, the alcohol which has been formed as a decomposition product of the ether also because the latter, due to its having been reacted nearly completely, is virtually absent from the reaction mixture. Once the alcohol has been withdrawn, the catalyst is reactivated again and it becomes thus possible to complete the reaction under the same conditions as before, by the transalkylation between the dialkylate and the phenolic substrate with the attendant formation of the monoalkylate which is generally the expected product. The absence of alcohol from the reactive mixture permits also the rearrangement of possible monoalkylated isomer towards the isomer which is thermodynamically stabler and which is generally speaking, the expected product.

EXAMPLE 1

1 mol of pyrocatechol (110 g) and 1.07 mol of methyl-terbutylether (MTBE) (94.2 g) are reacted in an autoclave in the presence of a quantity of Amberlyst 15 corresponding to 26.4 milliequivalents of H+ (5.5 g). The temperature is raised to 110° C. After two hours of reaction, the analysis of the product exhibits a conversion of MTBE equal to 92% and a conversion of the pyrocathecol as high as 74%, whereas the selectivity to 4-tert.butylpyrocatechol is 50% molar. Once the light products have been done away with by flashing and the temperature has been brought to 130° C., it has been observed that, after 2 hours, the conversion of pyrocatechol has risen to 94% with a selectivity to 4-tert.butyl-pyrocatechol as high as 90% molar.

EXAMPLE 2

The reaction is carried out with the same procedure as in the previous Example, with the exception that the catalyst is composed of sulphuric acid (26.4 milliequivalents, equal to 1.3 g of concentrated acid). After two hours of reaction, the conversion of MTBE is as high as 92% with a conversion of pyrocatechol of 71% and a selectivity to 4-tert.butyl pyrocatechol of 42% molar. Once the light fractions have been removed and the reaction mixture has been brought to 130° C., after two hours it is observed that the conversion of pyrocatechol has become 93% with a selectivity to the 4-tert.butyl-pyrocatechol as high as 90% mol.

EXAMPLE 3

1 mol of pyrocatechol (110 g) and 0.8 mol of MTBE (70.48 g) are reacted in the presence of a quantity of Amberlyst 15 equal to 26.4 milliequivalents of H+ (5.5 g). The temperature is raised to 110° C. After two hours of reaction, the conversion of MTBE is 99% and the conversion of pyrocatechol is 61% with a selectivity to 4-tert.butyl pyrocatechol equal to 55% molar. Once the light fractions have been flashed off and the temperature has been raised to 130° C. it is observed that, after two hours of reaction, the conversion of pyrocatechol has risen to 78% and the selectivity to 4-tert.butyl-pyrocatechol has rinse to 94% molar.

EXAMPLE 4

1 mol of pyrocatechol (110 g) and 0.8 mol of ethyl tert.butyl ether (ETBE) (81.6 g) are reacted in the presence of 5.5 g of Amberlyst 15 (26.4 milliequivalents of H+). The temperature is raised to 110° C. After 3 hours of reaction the conversion of ETBE is as high as 98% and the conversion of pyrocatechol is 60% with a selectivity to 4-tert.butylpyrocatechol equal to 62% molar. After having flashed off the light fractions which were formed, the temperature was raised to 130° C. After two hours it was observed that the conversion of pyrocatechol was as high as 75% and the selectivity to 4-tert.butylpyrocatechol rose to 94% molar.

EXAMPLE 5

1 mol of phenol (94 g) and 0.8 mol of MTBE (70.4 g) are reacted in the presence of a quantity of Lewasorb AC. 10 equal to 22.3 milliequivalents of H+ (5 g). The temperature is raised to 100° C. and after 3 hours it is observed that the conversion of MTBE is equal to 98% and the conversion of phenol is 51% with a selectivity to 4-tert.butylphenol of 33% molar. Once the light reaction products have been flashed off, the temperature is raised to 120° C. After 3 hours it is observed that the conversion of phenol has risen to 75% and the selectivity to 4-tert.butylphenol to 92% molar.

We claim:

1. In a process for the terbutylation of a phenolic compound by means of an alkyltert-butyl ether, comprising the steps of reacting in a first stage said phenolic compound in substantially stoichiometric ratios at a temperature comprised between 60° C. and 130° C. in the presence of a catalyst of acidic nature, the improvement consisting of removing the alcohol which is formed in said first stage and completing the reaction, after said alcohol removal, under substantially the same reaction conditions used in said first stage.

2. Process according to claim 1, characterized in that the terbutylation reaction is carried out with a quantity of catalyst equal to 5 to 50 milliequivalents of H+ per mol of the phenolic compound.

3. Process according to claim 1, characterized in that the phenolic compounds are members selected from the group consisting of phenol, pyrocatechol, hydroquinone.

4. Process according to claim 1, characterized in that the alkyl terbutyl ethers are selected from the group consisting of the compounds having the formula:

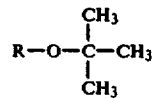

wherein R is a primary or a secondary alkyl group.

* * * * *